United States Patent
Carrasco-Zevallos et al.

(10) Patent No.: US 10,660,519 B2
(45) Date of Patent: May 26, 2020

(54) SYSTEMS AND METHODS FOR EYE TRACKING FOR MOTION CORRECTED OPHTHALMIC OPTICAL COHERENCE TOMOGRAPHY

(71) Applicant: Duke University, Durham, NC (US)

(72) Inventors: Oscar M. Carrasco-Zevallos, Durham, NC (US); Joseph A. Izatt, Durham, NC (US); Christian B. Viehland, Durham, NC (US); Ryan McNabb, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/113,800

(22) PCT Filed: Jan. 30, 2015

(86) PCT No.: PCT/US2015/013870
§ 371 (c)(1),
(2) Date: Jul. 22, 2016

(87) PCT Pub. No.: WO2015/116981
PCT Pub. Date: Aug. 6, 2015

(65) Prior Publication Data
US 2016/0338589 A1    Nov. 24, 2016

Related U.S. Application Data

(60) Provisional application No. 61/933,529, filed on Jan. 30, 2014.

(51) Int. Cl.
*A61B 3/14* (2006.01)
*A61B 3/15* (2006.01)
(Continued)

(52) U.S. Cl.
CPC .............. *A61B 3/152* (2013.01); *A61B 3/102* (2013.01); *A61B 3/113* (2013.01); *A61B 3/117* (2013.01); *A61B 3/1225* (2013.01)

(58) Field of Classification Search
CPC .. G01N 2021/1787; A61F 2009/00846; G01L 39/02091; G06T 2207/10101;
(Continued)

(56) References Cited

U.S. PATENT DOCUMENTS 5,537,162 A * 7/1996 Hellmuth ............... A61B 3/102
351/206
2005/0270486 A1    12/2005 Teiwes et al.
(Continued)

OTHER PUBLICATIONS

Lujan, Brandon J., et al., Revealing Henle's Fiber Layer Using Spectral Domain Optical Coherence Tomography, Investigative Ophthalmology & Visual Science, Mar. 2011, vol. 52, No. 3, 2011.
(Continued)

*Primary Examiner* — Mahidere S Sahle
(74) *Attorney, Agent, or Firm* — Olive Law Group, PLLC

(57) ABSTRACT

Systems and methods for eye tracking for motion corrected ophthalmic optical coherence tomography (OCT) are disclosed. According to an aspect, an imaging system includes an eye tracking device configured to determine movement of an eye. The imaging system also includes an OCT apparatus configured to generate OCT images of a retina of the eye. The OCT apparatus includes a scanner operable to be moved for relocating an OCT scan pivot at a pupil plane for image capture and during capture of the OCT images. The imaging system also includes a controller configured to control the scanner to relocate the OCT scan pivot at the pupil plane based on the determined movement of the eye.

14 Claims, 13 Drawing Sheets

(51) Int. Cl.
*A61B 3/10* (2006.01)
*A61B 3/113* (2006.01)
*A61B 3/117* (2006.01)
*A61B 3/12* (2006.01)

(58) Field of Classification Search
CPC .......... G06T 2207/30041; A61B 3/102; A61B 3/113; G01B 9/02091
USPC ......................................................... 351/209
See application file for complete search history.

(56) References Cited

U.S. PATENT DOCUMENTS

| | | | |
|---|---|---|---|
| 2007/0252951 A1* | 11/2007 | Hammer | A61F 9/008 351/221 |
| 2009/0244485 A1 | 10/2009 | Walsh et al. | |
| 2011/0043757 A1 | 2/2011 | Everett et al. | |
| 2011/0234978 A1* | 9/2011 | Hammer | A61B 3/102 351/208 |
| 2013/0010259 A1 | 1/2013 | Carnevale | |
| 2013/0016319 A1 | 1/2013 | Vohnsen et al. | |
| 2013/0188140 A1 | 7/2013 | Bagherinia et al. | |
| 2013/0293838 A1 | 11/2013 | Makihira et al. | |
| 2014/0009741 A1 | 1/2014 | Levien et al. | |
| 2014/0247425 A1 | 9/2014 | Hammer et al. | |

OTHER PUBLICATIONS

PCT International Search Report for PCT International Application No. PCT/US15/13870.

PCT International Written Opinion for PCT International Application No. PCT/US15/13870.

Dabov, Kostadin et al., Image Denoising by Sparse 3-D Transform-Domain Collaborative Filtering, IEEE Transactions on Image Processing, vol. 16, No. 8, Aug. 2007.

Dhalla, Al-Hafeez et al., Complex Conjugate Resolved Heterodyne Swept Source Optical Coherence Tomography Using Coherenece Revival, Biomedical Optics Express, vol. 3, No. 3, Feb. 24, 2012.

Ferguson, R. Deniel et al., Tracking Optical Coherence Tomography, Optics Letters, vol. 29, No. 18, Sep. 15, 2004.

Hendargo, Hansford C. et al., Automated Non-Rigid Registration and Mosaicing for Robust Imaging of Distinct Retinal Capillary Beds Using Speckle Variance Optical Coherence Tomography, Biomedical Optics Express, vol. 4, No. 6, May 7, 2013.

Martinez-Conde, Susan et al., The Role of Fixational Eye Movements in Visual Perception, Nature Reviews, Neuroscience, vol. 5, pp. 229-240, Mar. 2004.

McNabb, Ryan P. et al., Distributed Scanning Volumetric SDOCT for MOtion Corrected Corneal Biometry, Biomedical Optics Express, vol. 3, No. 9, Aug. 10, 2012.

Ji, Na et al., Adaptive Optics Via Pupil Segmentation for High-Resolution Imaging in Biological Tissues, Nature Methods, vol. 7, No. 2, Feb. 2010.

Wieser, Wolfgang et al., Multi-Megahertz OCT: High Quality 3D Imaging at 20 Million A-Scans and 4.5 GVoxels Per Second, Optics Express, vol. 18, No. 14, Jun. 30, 2010.

Liao, Wen-Hung et al., Robust Pupil Detection for Gaze-Based User Interface, EGIHMI, Feb. 7, 2010.

Pircher, Michael et al., Simultaneous SLO/OCT Imaging of the Human Retina with Axial Eye Motion Correction, Optics Express, vol. 15, No. 25, Dec. 4, 2007.

International Preliminary Report on Patentability issued in PCT Application No. PCT/US2015/013870 dated Aug. 2, 2016.

* cited by examiner

FIG. 13A
FIG. 13B
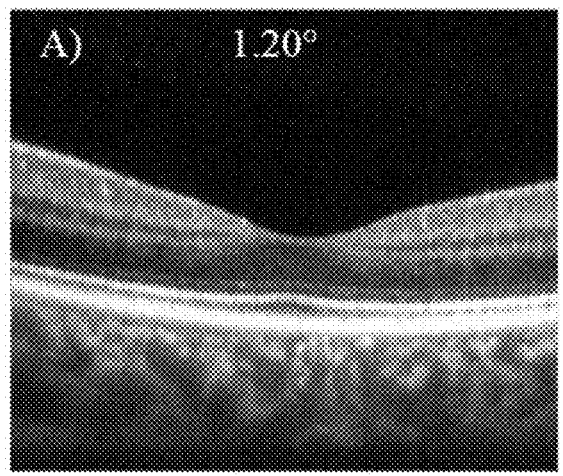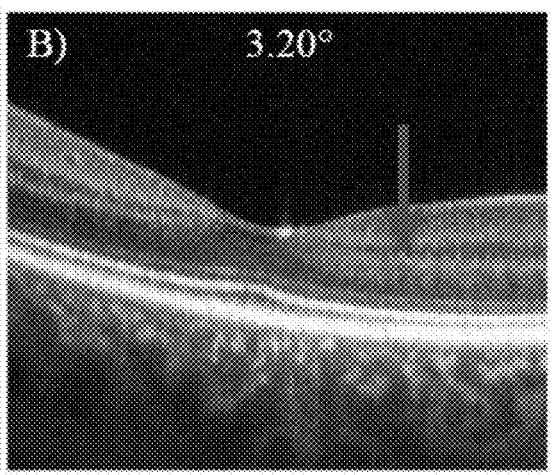
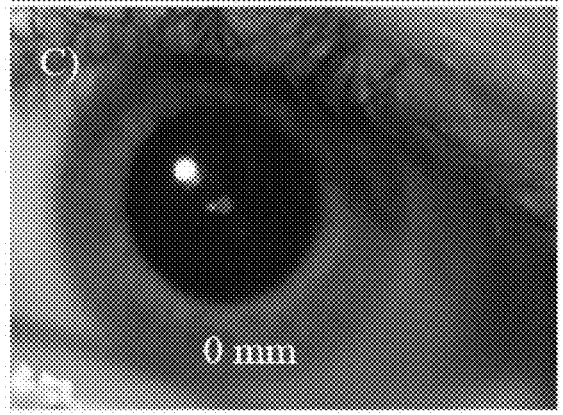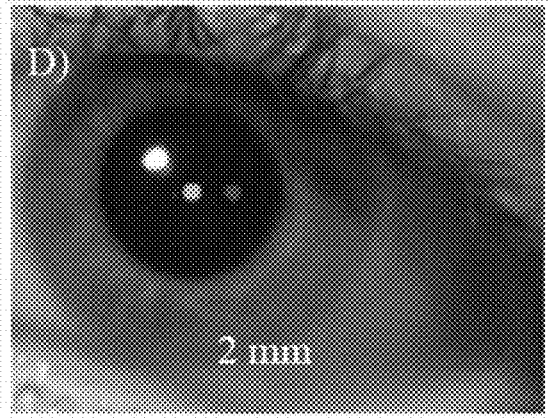
FIG. 13C
FIG. 13D

SYSTEMS AND METHODS FOR EYE TRACKING FOR MOTION CORRECTED OPHTHALMIC OPTICAL COHERENCE TOMOGRAPHY

CROSS REFERENCE TO RELATED APPLICATIONS

This application is a 35 USC 371 application of International PCT Patent Application No. PCT/US2015/013870, filed on Jan. 30, 2015, and titled SYSTEMS AND METHODS FOR EYE TRACKING FOR MOTION CORRECTED OPHTHALMIC OPTICAL COHERENCE TOMOGRAPHY, which claims priority to U.S. Provisional Patent Application No. 61/933,529, filed Jan. 30, 2014 and titled PUPIL TRACKING FOR MOTION CORRECTED OPHTHALMIC OPTICAL COHERENCE TOMOGRAPHY, the disclosure of which is incorporated herein by reference in its entirety.

GOVERNMENT RIGHTS NOTICE

This invention was made in part with government support by the United States government under Federal Grant Number EY023039, awarded by the National Institute of Health (NIH). Accordingly, the government has certain rights in the invention.

TECHNICAL FIELD

The presently disclosed subject matter relates to medical devices. Particularly, the presently disclosed subject matter relates to systems and method for eye tracking for motion corrected ophthalmic optical coherence tomography.

BACKGROUND

Optical coherence tomography (OCT) has become the standard of care for diagnosis and following treatment of many pathological ophthalmic conditions in the posterior and anterior human eye. However, conventional OCT systems do not capture volumes instantaneously and are therefore subject to artifacts due to patient motion. While a subject's voluntary motion may be mitigated with a fixation target, involuntary motion such as micro-saccades, drifts, or tremors may still corrupt OCT volumetric data and associated en face summed volume projections (SVPs). In previous work, real-time tracking for motion compensated OCT has focused on retinal imaging. However, as the clinical prominence of volumetric anterior segment OCT increases, the need for real-time motion-correction solutions designed for anterior segment imaging has become apparent.

Conventional OCT retinal imaging systems employ a telescope to image the beam scanning pivot onto the pupil plane of the patient. To maximize collection efficiency of back-scattered light and to minimize aberrations and vignetting, the scanning beam should optimally rotate through the central cornea, and the scan pivot should be imaged at the center of the ocular pupil. Moreover, specific retinal features, such as the cone photoreceptors and Henle's Fiber Layer (HFL), exhibit back-reflected intensity dependence on pupil entry position. Commercial OCT systems employ an infrared (IR) pupil camera to allow alignment of the OCT beam onto the patient's eye and to vary pupil entry position. However, such systems are still vulnerable to lateral patient motion and depend upon active involvement of the photographer to obtain and maintain alignment.

In view of the foregoing, there is a desire to provide improved OCT systems and methods for retinal imaging.

BRIEF SUMMARY

Disclosed herein are OCT systems and methods that mitigate lateral motion artifacts in both anterior segment and retinal OCT imaging by tracking the ocular pupil. More particularly, systems and methods for eye tracking for motion corrected ophthalmic OCT are disclosed. According to an aspect, an imaging system includes an eye tracking device configured to determine movement of an eye. The imaging system also includes an OCT apparatus configured to generate OCT images of a retina of the eye. The OCT apparatus includes a scanner operable to be moved for relocating an OCT scan pivot at a pupil plane for image capture and during capture of the OCT images. The imaging system also includes a controller configured to control the scanner to relocate the OCT scan pivot at the pupil plane based on the determined movement of the eye.

According to another aspect, an imaging system includes an eye tracking device configured to determine movement of an eye. The imaging system also includes an OCT apparatus configured to generate OCT images of an anterior segment of the eye. The OCT apparatus includes a scanner operable to be moved for relocating an OCT scan at a system image plane during capture of the OCT images. Further, the imaging system includes a controller configured to control the scanner to relocate the OCT scan at the system image plane based on the determined movement of the eye.

BRIEF DESCRIPTION OF THE SEVERAL VIEWS OF THE DRAWINGS

The foregoing aspects and other features of the present subject matter are explained in the following description, taken in connection with the accompanying drawings, wherein:

FIGS. 13A-13D shows two averaged (20×) B-scans acquired at different pupil entry positions.

DETAILED DESCRIPTION

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "an" and "an" are used herein to refer to one or more than one (i.e., at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

In accordance with embodiments, the imaging systems and methods disclosed herein may be used for determining ocular pupil movement or location during OCT imaging of the anterior segment or retina. The pupil movement or location can be utilized to control one or more lateral scanners or steering mirrors in the sample arm optical path of the OCT apparatus during anterior segment or retinal imaging. As a result, lateral motion artifacts in both anterior segment and retinal OCT can be mitigated. Such lateral motion artifacts can be due to patient motion. While a patient's voluntary motion may be mitigated with a fixation target, involuntary motion, such as micro-saccades, drifts, or tremors, may still corrupt OCT volumetric data and associated en face summed volume projections (SVPs). Furthermore, operator misalignment and patient movement may cause coarse, lateral translation of the eye relative to the OCT beam path. The presently disclosed subject matter can be used to reduce motion artifacts in anterior segment OCT by tracking the movement or location of the pupil and correcting for the motion by making use of one or more scanning mirrors.

Figure 1:
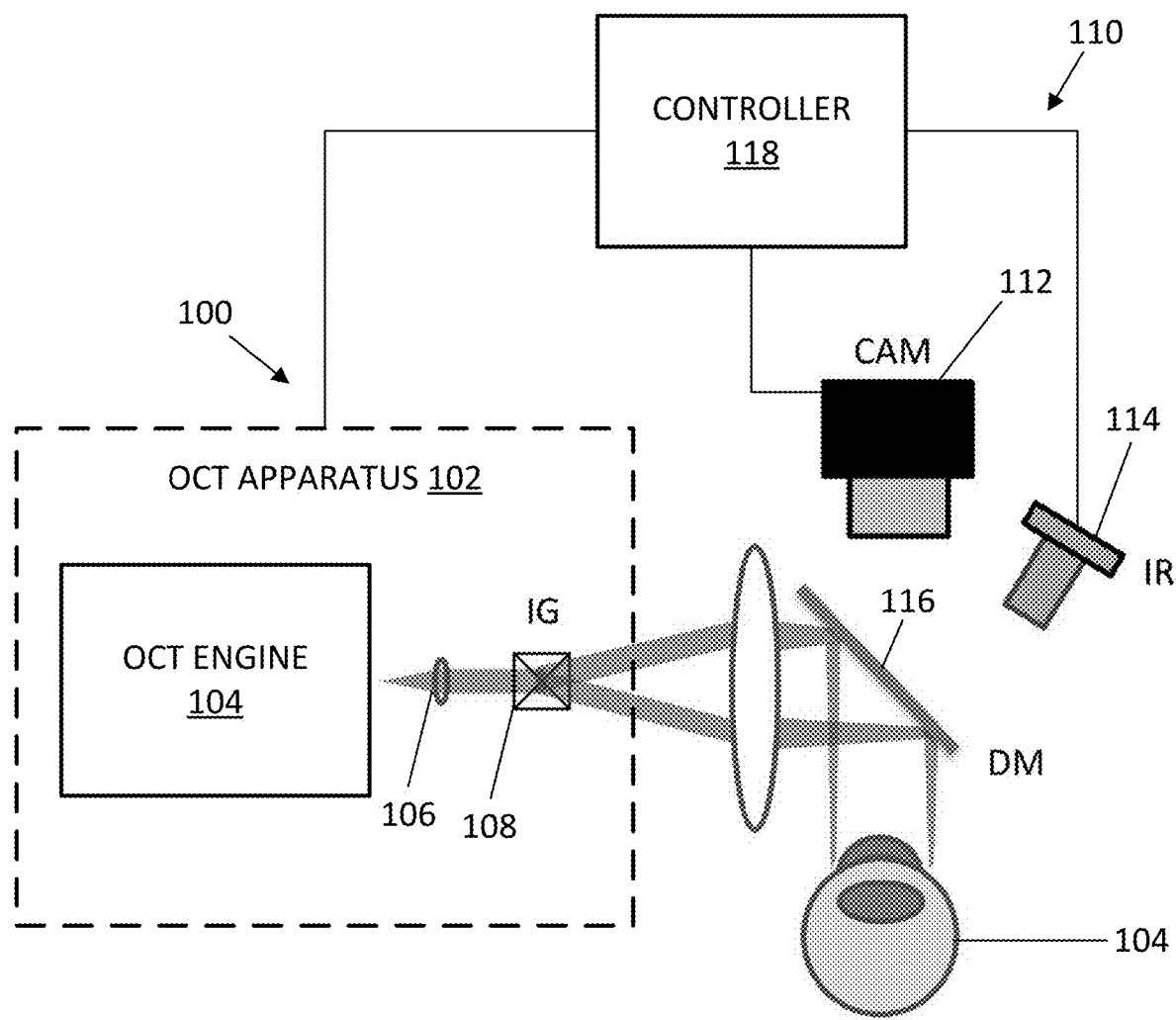
FIG. 1 is a schematic diagram of an example imaging system in accordance with embodiments of the present disclosure.

FIG. 1 illustrates a schematic diagram of an example imaging system 100 in accordance with embodiments of the present disclosure. This system may be used for imaging of the anterior segment. Referring to FIG. 1, the imaging system 100 may include an OCT apparatus 102 configured to generate OCT images of an eye 104. The OCT apparatus 102 may include an OCT engine 104, a lens 106, and an imaging galvanometer 108. Any suitable OCT engine may be utilized as will be understood by those of skill in the art.

Figure 2:
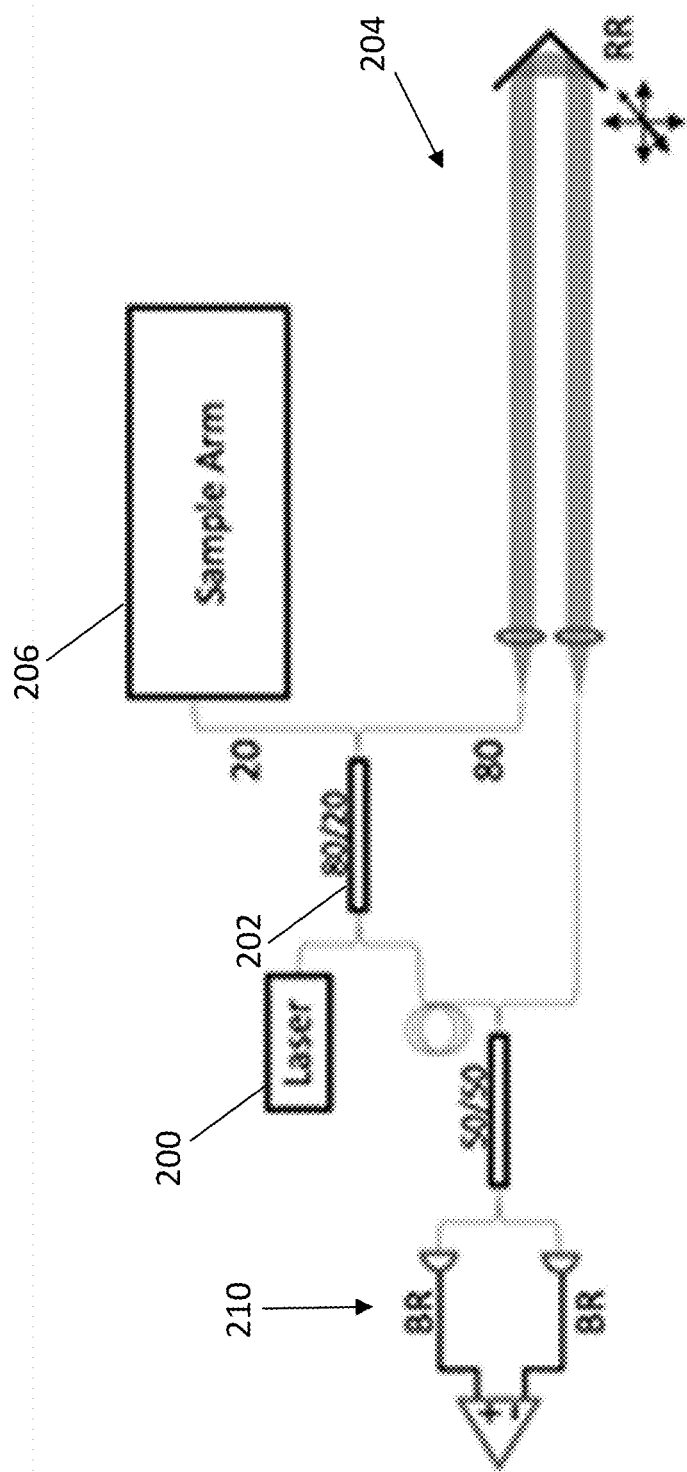
FIG. 2 is a schematic diagram of an example OCT engine in accordance with embodiments of the present disclosure.

FIG. 2 illustrates a schematic diagram of an example OCT engine 104 in accordance with embodiments of the present disclosure. The OCT engine 104 in this example is a swept-source OCT (SSOCT) engine, although it should be understood that any suitable type of OCT engine may be utilized. This example OCT engine 104 may be used together with any of the other examples disclose herein, such as in place of the OCT engine 104 shown in FIG. 2, more detail of which follows.

Referring to FIG. 2, the OCT engine 104 may include a laser 200. As an example, the laser 200 may be a swept-frequency laser centered at 1040 nm, with a tuning bandwidth of 100 nm and a repetition rate of 100 kHz for illuminating a Mach-Zehneder interferometer 202. Light returning from the reference arm 204 and sample arm 206 may be collected with a balanced receiver 210 (such as a receiver manufactured by Thorlabs, Inc., of Newton, N.J.). A digitizer (such as a digitizer manufactured by AlazarTech, Inc., of Pointe-Claire, QC, Canada) may digitize the interferometric signal and the k-clock from the swept source. The OCT system may be controlled by suitably-configured software. In experimentation in a retinal imaging configuration, the system achieved a depth range of 3.7 mm and a peak sensitivity of 101 dB.

The imaging system 100 may include an eye tracking device 110 configured to determined movement of an eye. For example now turning to FIG. 1, the imaging system 100 includes a camera 112 positioned and configured to capture a sequence of images or video of the eye 104. Video of the pupil of the eye 104 may be obtained, for example, using a high-speed camera (e.g., Edmund Optics USB 3.0 Machine Vision Camera, Edmund Optics; Barrington, N.J.) with a maximum frame rate of 100 frames per second (FPS). The eye tracking device 110 may also include a light source 114 such as, but not limited to, a light emitting diode (LED). In an example, the eye 104 may be illuminated with an 850 nm LED (e.g., an LED available from Thorlabs, of Newton, N.J.). To co-align the infrared (IR) illumination with the optical axis of the OCT system, the camera 112 and light source 114 may be placed behind a short-pass dichroic mirror 116 with a cutoff at 960 nm. The IR illumination may be transmitted through the pupil. In addition, the IR illumination may be reflected by the iris, sclera, and the surrounding skin yielding images with a bi-modal histogram that allowed for segmentation.

The imaging system 100 may include a controller 118 for processing images captured by the eye tracking device 110. For example, the controller 118 may include suitable hardware, software, firmware, or combinations thereof for implementing the functionality described herein. The functions may be implemented by one or more processors and memory, for example. The controller 118 may, utilizing the bi-model histogram, threshold the images to produce binary images for initial pupil tracing. Morphological operations may be used to remove extraneous dark regions (i.e., shadows or eyelashes) and to smooth the boundary of the pupil. The controller 118 may utilize connected component analysis to identify the pupil center. In real-time operation, an algorithm implemented by the controller 118 indicate the location of the pupil center in the displayed image and outputs pupil movement relative to the previous frame. This approach is fast and can work extremely well for the bimodal images produced by the controlled IR illumination. In an example, this eye tracking may be performed on a separate computer from the OCT apparatus 102. The tracking frame rate may be estimated by timing the pupil tracking video and counting the number of tracked frames.

Figure 3:
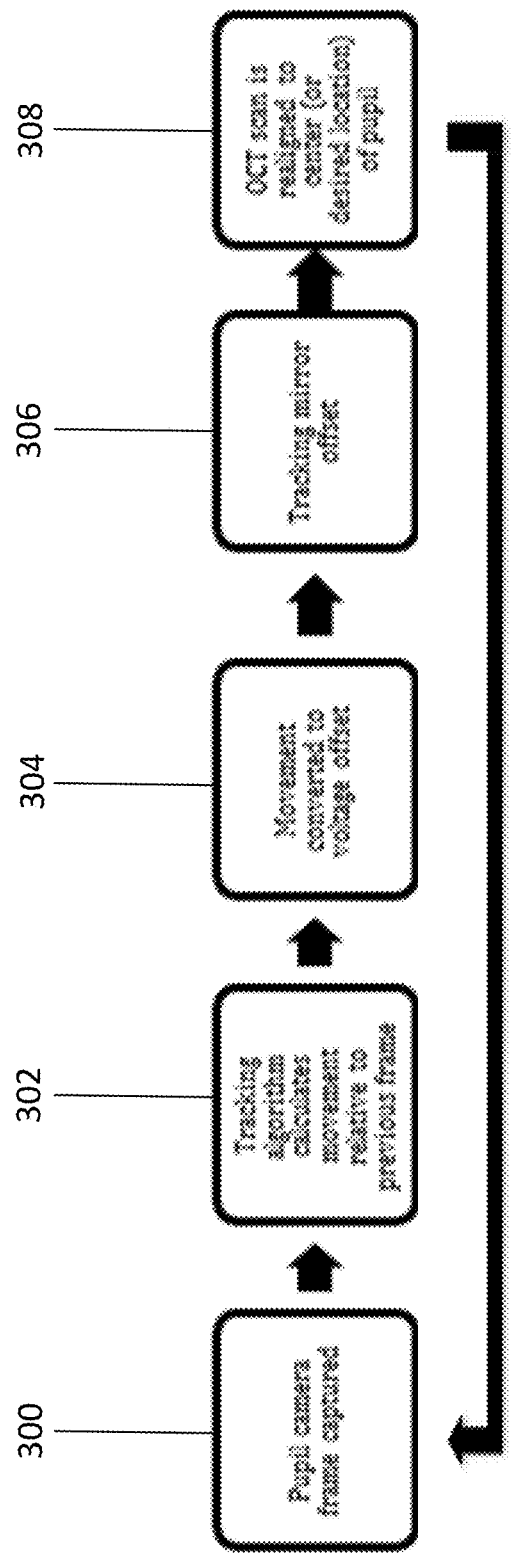
FIG. 3 is a flow chart of an example method for pupil tracking in accordance with embodiments of the present disclosure.

FIG. 3 illustrates a flow chart of an example method for pupil tracking in accordance with embodiments of the present disclosure. The example method is described as being implemented by the imaging system 100 shown in FIG. 1, although it should be understood that the method may be implemented by any suitable imaging system having an eye tracking device. It is also noted that the steps of the method may be implemented recursively.

Referring to FIG. 3, the method includes capturing 300 a frame or image. For example, the camera 112 may capture an image of the pupil of the eye 104. The image may be one in a sequence of images or video captured by the camera 112. The captured image 112 may be received by the controller 118.

Continuing with FIG. 3, the method includes calculating 302 movement relative to a previous frame. As an example, the controller 118 may calculate movement of the pupil of the eye 104 by comparing the captured image to a previously-captured image. Subsequently, the method includes converting 304 movement to voltage offset. More particularly, for example, an output may be produced that is an offset of the center of the pupil in terms of pixels of the pupil camera. The controller 118 may convert this offset to a pair of offset voltages for a tracking mirrors 306 of the OCT apparatus 102. The mirrors may be moved based on the offset voltages. The method includes subsequently realigning 308 the OCT scan to center (or another desired feature or location) of the pupil. Subsequently, the method may return to step 300.

In an example of controlling mirrors, the imaging galvanometer 108 of the OCT apparatus of FIG. 1 may include scanning mirrors that are controllable by the controller 118. The anterior segment sample arm configuration has a telecentric scanning design, as depicted in FIG. 1. The x-y galvanometer scanning mirror pair may also function as the tracking mirrors for lateral motion compensation. The voltage offsets may be summed with the galvanometer scanning voltage waveform from the OCT control software via a summing amplifier analog circuit. The voltage offsets may laterally displace the OCT scan to compensate for lateral pupil motion and enable motion-corrected volumetric OCT images.

Figure 4:
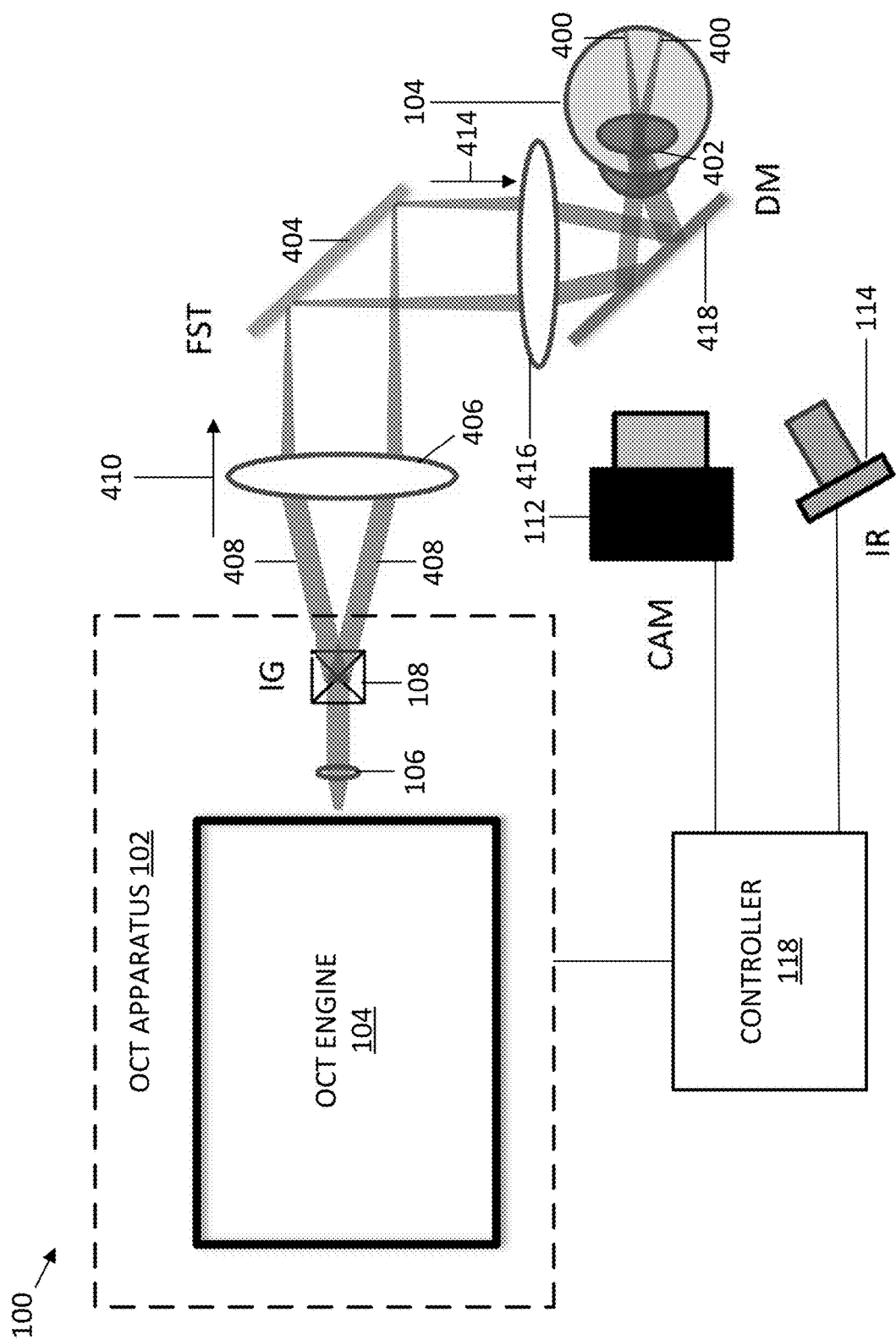
FIG. 4 is a schematic diagram of another example imaging system 100 in accordance with embodiments of the present disclosure.

FIG. 4 illustrates a schematic diagram of another example imaging system 100 in accordance with embodiments of the present disclosure. Referring to FIG. 4, the imaging system 100 may include an OCT apparatus 102 configured to generate OCT images of a retina of an eye 104 of a subject or patient undergoing examination. This example provides an example configuration for retinal imaging, although it should be understood that there are other suitable configurations as well. The OCT apparatus 102 includes an OCT engine 104, a lens 106, and an imaging galvanometer 108.

The imaging system 100 also includes an eye tracking device 110 configured to determine movement of the eye 104. More particularly, the eye tracking device 110 includes a camera 112 and light source 114. The eye tracking device 110 may be controlled by the controller 118 for activating the light source 114 and for operating the camera 112.

The imaging system 100 shown in FIG. 1 may be used for retinal scanning and may employ a 4f topology with the incident beam location at the edges of the scan range depicted by reference number 400 and along the optic axis. The scanner may be configured for live or real-time tracking of the pupil. The pupil is indicated by reference number 402. Eye rotation causes both rotation and lateral translation of the pupil, since the axis of eye rotation does not coincide with the location of the ocular pupil. The imaging system 100 of FIG. 1 may be utilized to overcome difficulties with imaging when the eye rotates or translates laterally. Example difficulties includes vignetting or aberrations of the OCT beam due to the lateral translation of the pupil inherent to eye rotation. As a consequence, the uncompensated lateral translation due to eye rotation can introduce aberrations and vignetting if it is not properly compensated for. Further, pure lateral translation, commonly caused by operator misalignment and course patient movement, can cause severe vignetting and/or introduce aberrations. Only tracking of the ocular pupil can provide the information necessary to compensate for purely translation pupil movement. Moreover, specific retinal structures exhibit back-reflected intensity dependence on pupil entry position.

Turning to FIG. 4, the imaging system 100 is configured for retinal imaging. The imaging system 100 includes a tracking mirror 404. For example, the tracking mirror 404 may be a fast 2-D steering mirror (FST) (e.g., available from Optics in Motion, of Long Beach, Calif.) having a bandwidth of 760 Hz. Using a 4f scanning topology, the mirror 404 was placed in a plane conjugate to the imaging plane. Therefore, angular scanning of the mirror 404 results in lateral displacement of the image of the galvanometer scanning mirrors of the imaging galvanometer 108. The galvanometers may be imaged onto the ocular pupil. Lateral patient movement can result in vignetting of the OCT retinal image. Lateral pupil tracking using the FST can mitigate vignetting by ensuring that the scanning mirrors are always imaged onto the ocular pupil and precisely control the pupil entry location.

The eye tracking device 110 may include a lens 406 positioned in a first position downstream from light 408 generated by the OCT apparatus and configured to pass the generated light along a direction generally indicated by arrow 410. The mirror 404 may be a fast steering mirror positioned to intercept the light passing along the direction 410 and configured to re-direct the generated light in another direction generally indicated by arrow 414. The eye tracking device 110 may include another lens 416 positioned to intercept the light re-directed in the direction 414 and configured to pass the re-directed light. The eye tracking device 110 may include a dichroic mirror 418 positioned to receive the light from the lens 416 and configured to re-direct the light towards the eye 104. The eye tracking device 110 can determine movement of the pupil of the eye 104. The controller 118 can control the mirror 404 based on the determined movement of the pupil during retinal imaging.

Figure 5A:
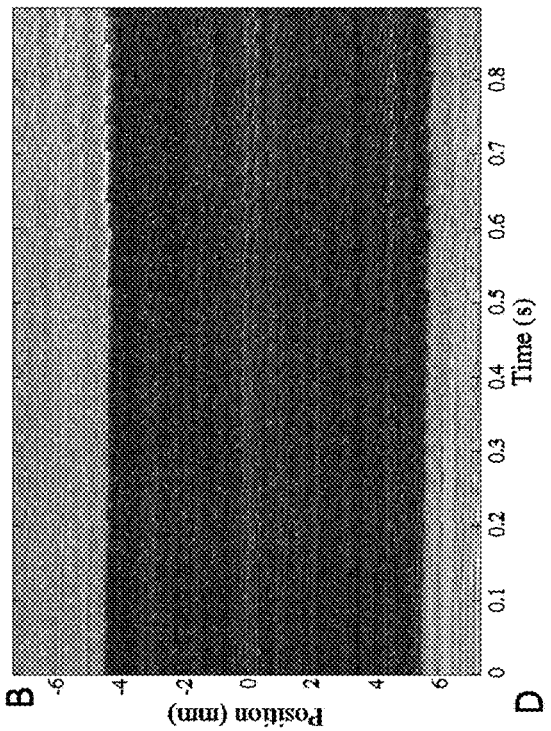
FIGS. 5A and 5B are images of untracked and tracked b-scan sequences with simulated motion.
Figure 5B:
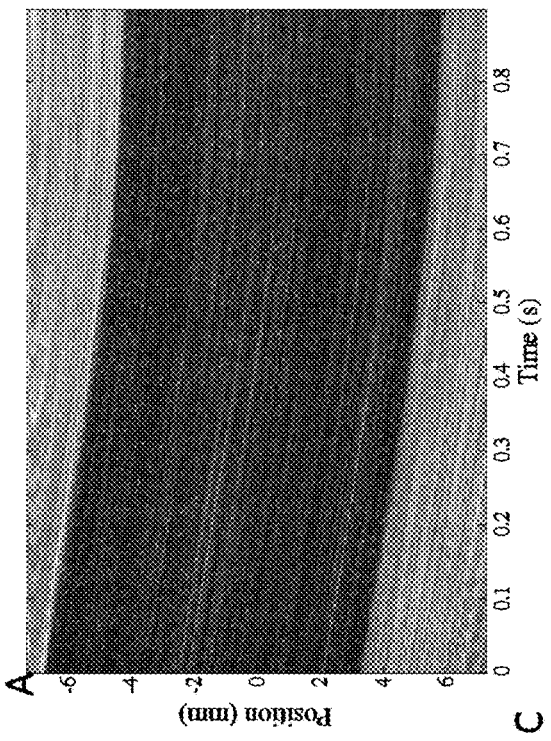
Figure 5C:
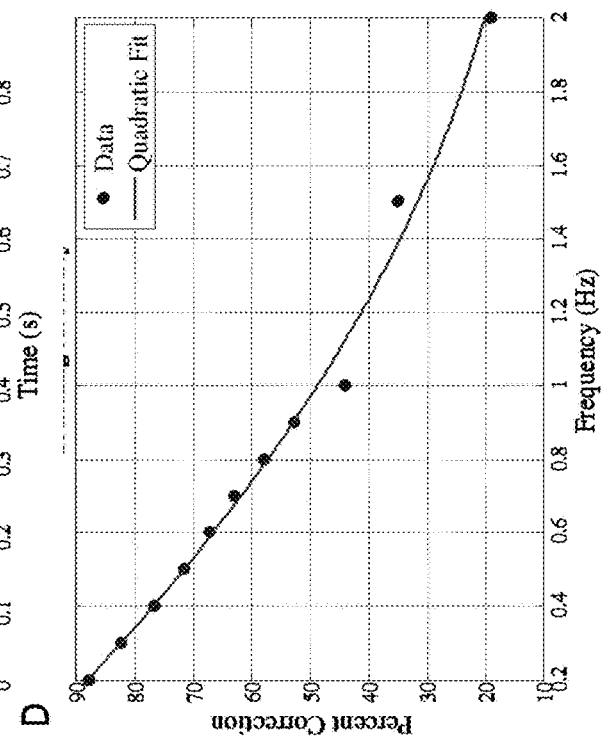
FIG. 5C is a graph showing motion with and without tracking.
Figure 5D:
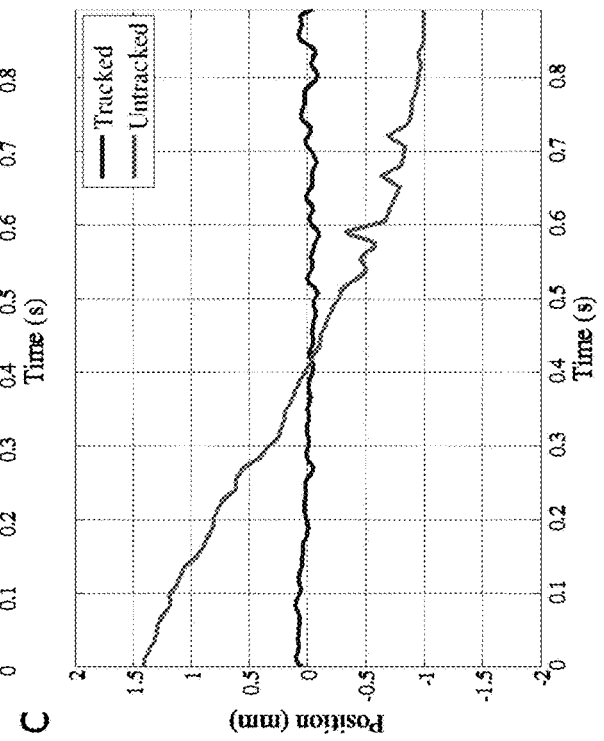
FIG. 5D is a graph showing tracking accuracy versus frequency of simulated motion.

To demonstrate real-time pupil motion compensation, in vivo OCT retinal and anterior segment images of human volunteers were acquired. The sample arm optics were mounted on a joystick-adjustable slit-lamp base to help with patient alignment. The pupil tracking algorithm was characterized by imaging a pupil phantom in the anterior segment configuration. A fast 2-D steering mirror with a bandwidth of 760 Hz was placed between the OCT objective lens and the model eye to simulate motion with precise amplitude and frequency along the OCT fast-axis. With and without tracking, repeated B-scans composed of 300 A-scans per B-scan at a rate of ~330 B-scans per second with the steering mirror providing simulated motion of varying frequencies and constant amplitude (2.5 mm) were acquired. The SVP of the set of B-scans was displayed in sequence, as shown in FIGS. 5A and 5B for simulated motion of 0.3 Hz. From each tracked and untracked B-scan sequence, the image gradient was calculated to extract the edge of the pupil phantom (black) from the background (white). FIG. 5C shows motion as a function of time corresponding to 0.3 Hz of applied simulated motion. Motion correction accuracy was calculated by subtracting the standard deviation (stdev) of untracked motion by the stdev of tracked motion, and dividing the result by the stdev of the untracked motion (FIG. 5D). Perfect motion tracking may result in zero stdev for the motion tracked scenario and thus 100% motion correction. Motion correction accuracy was calculated for up to 2 Hz simulated motion.

The gradient operator utilized to calculate motion is subject to speckle noise and may yield outliers as evidenced by the three peaks in the green plot in FIG. 5C. However, these outliers were rare and thus had little influence on the standard deviation calculations. From FIG. 5D, the ~3 dB threshold for motion correction is at about 1 Hz for simulation motion of 2.5 mm. In its current iteration, real-time pupil tracking is suitable for correcting large patient motion caused by operator misalignment and poor fixation. The latency of the pupil tracking system was calculated to be ~100 ms by measuring the phase delay between the start of the simulated movement and correction signals sent to the scanning mirrors. Therefore, although this example tracking algorithm can achieve a frame rate of 37 fps, the frequency of motion corrected by the system is currently limited by latency.

Figures 6A, 6B, 6C:
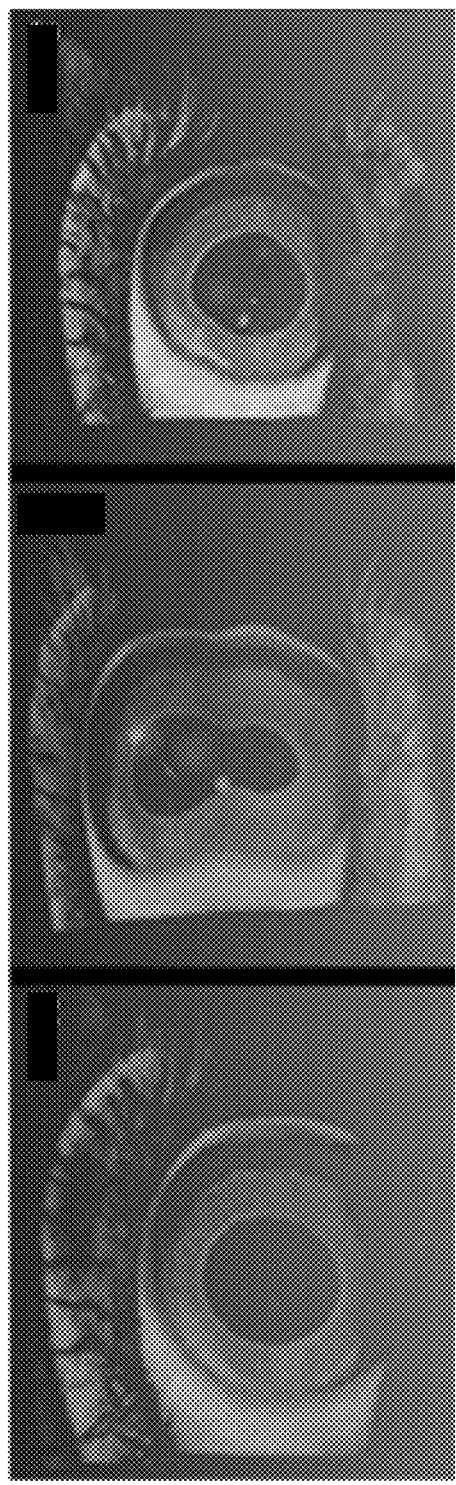
FIG. 6A is an image with the volume acquired with no patient motion and no correction.
FIG. 6B is an image showing deformation due to patient motion.
FIG. 6C is an image showing that motion artifacts were mitigated in real-time with pupil tracking.
Figures 7A, 7B, 7C, 7D:
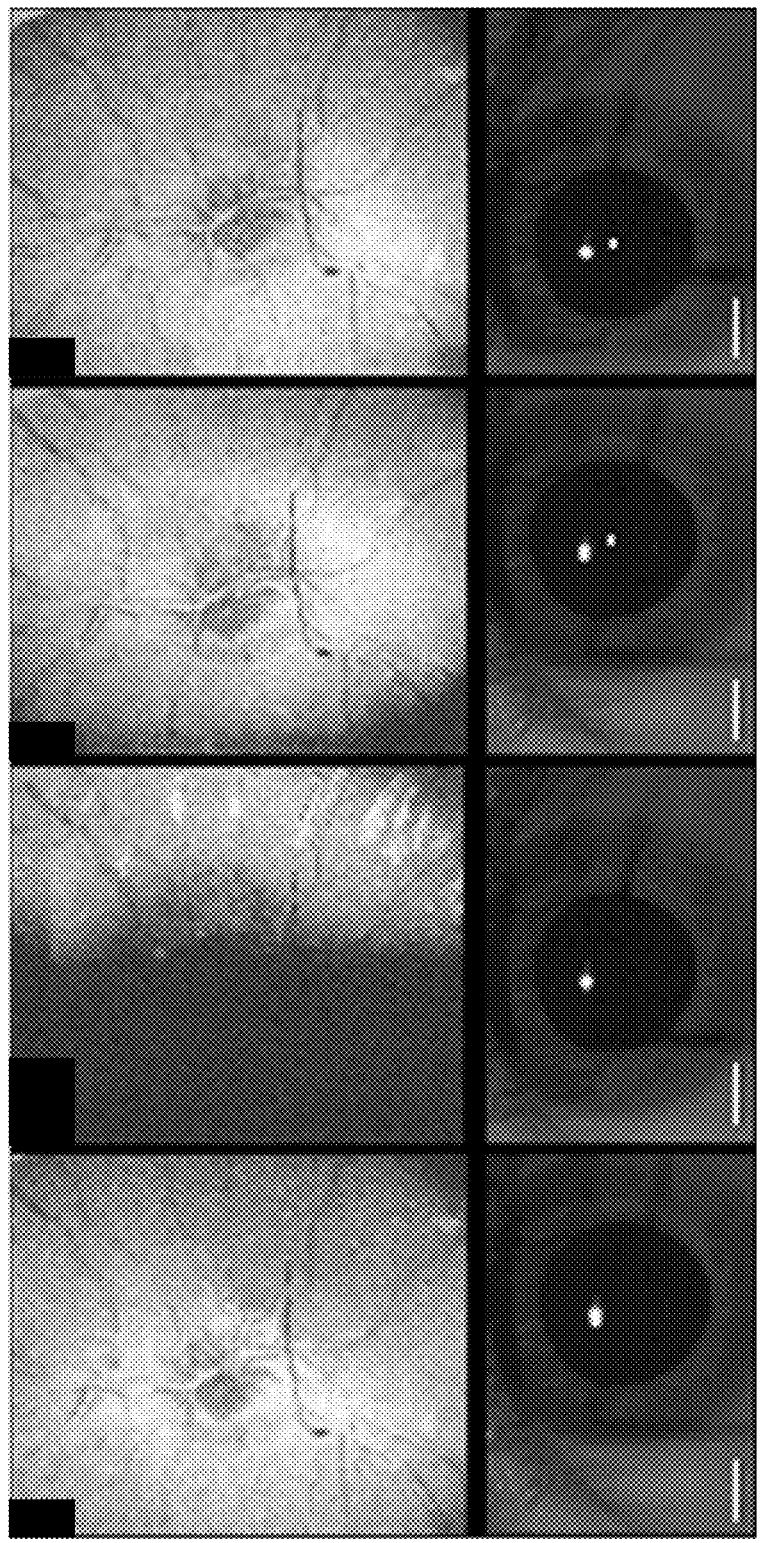
FIGS. 7A-7D are images showing summed volume projections from OCT volumetric images with and without pupil tracking.

Anterior segment in vivo volumetric OCT images using the sample arm depicted in FIGS. 6A-6C were acquired with and without tracking. To simulate patient motion, the subject was asked to talk during OCT volume acquisition. Prior to volumetric rendering, each OCT image was denoised utilizing BM3D. Complex conjugate removal with coherence revival enabled visualization of the entire anterior segment. The scan dimensions were 15×15 mm. FIG. 6A depicts an image with the volume acquired with no patient motion and no correction. Patient motion resulted in significant deformation of the image, noted for example by the elongated shape of the ocular pupil in FIG. 6B. Motion artifacts were mitigated in real-time with pupil tracking, as shown in FIG. 6C.

To demonstrate the utility of pupil tracking in retinal configuration, +/−8 degree in vivo volumetric retinal OCT images were acquired with patient motion using a suitable sample arm. Moving the slit-lamp base laterally simulated patient motion. FIGS. 7A-7D are images showing summed volume projections (SVP) from OCT volumetric images with and without pupil tracking. The corresponding frames from the pupil camera are below each SVP. As shown in FIG. 6B, lateral pupil motion results in significant vignetting.

Figures 8A, 8B:
FIGS. 8A and 8B are images showing registered and averaged (50 frames) b-scans without (FIG. 8A) and with (FIG. 8B) tracking.

Real-time tracking of the ocular pupil and motion compensation with the FST mitigates vignetting, as shown in FIG. 6D. FIGS. 8A and 8B are images showing registered and averaged (50 frames) b-scans without (FIG. 8A) and with (FIG. 8B) tracking. Note the signal-to-noise ratio (SNR) drop in at the scan edges of the untracked b-scan due to vignetting.

Figure 9:
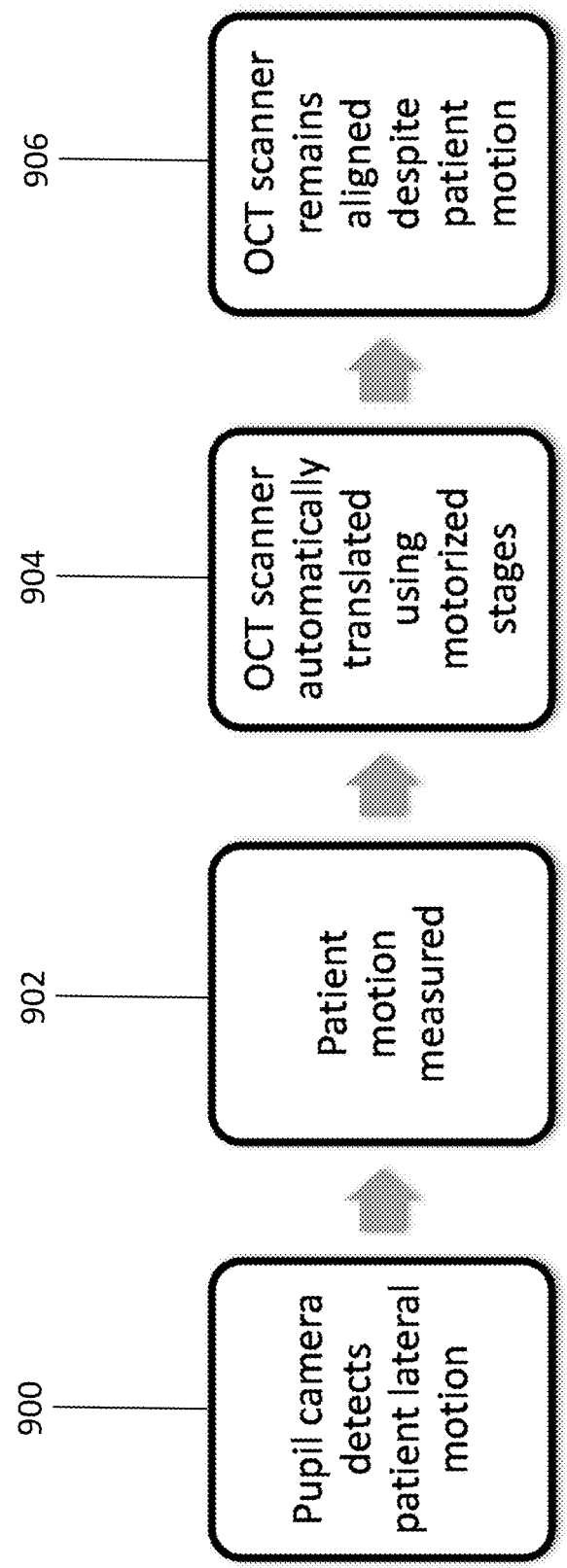
FIG. 9 is a flow chart of an example method for aligning an OCT scanner in accordance with embodiments of the present disclosure.

In accordance with embodiments of the present disclosure, an OCT scanner can be automatically adjusted or moved based on detected patient pupil movement and overall patient movement. The OCT sample arm scanner can be repositioned laterally using motorized translational stages. FIG. 9 illustrates a flow chart of an example method for aligning an OCT scanner in accordance with embodiments of the present disclosure. Referring to FIG. 9, a camera may capture a sequence of images of a pupil of a patient. A controller as disclosed herein may detect 900 patient lateral motion based on the captures images. The method includes measuring 902 patient motion using an eye tracking device. The method also includes using 904 motorized stages of the OCT scanner to automatically translate based on the detected patient lateral motion and the patient motion. Further, the method includes aligning 906 the OCT scanner despite the patient motion. During this process, the OCT scanner is kept aligned by movement of the OCT scanner and during generation of OCT images.

In accordance with embodiments, systems and methods are disclosed for controlling the lateral pupil entry position by utilizing automated pupil tracking in conjunction with a 2D fast steering mirror conjugate to the retinal plane. Such systems and methods can facilitate OCT studies concerning directional sensitivity of retinal structures by automating translation of the pupil entry position.

Pupil entry position can be important in all forms of retinal imaging. Poor off axis retinal reflectivity can be attributed to the Stiles-Crawford effect, the waveguiding effect of cone photoreceptors, and can result in poor imaging performance when pupil position is not well controlled. The Stiles-Crawford effect has been previously investigated with OCT by measuring the dependence of backscattered intensity from the IS/OS, PTOS, and RPE retinal layers as a function of pupil entry position. In studies, the pupil entry position was varied manually and was subject to lateral motion artifacts. Henle's Fiber Layer (HFL) is an additional retinal layer which exhibits reflectivity dependence on pupil entry position. It was discovered that the oblique orientation of HFL around the foveal pit resulted in a loss of OCT visualization if the beam scanning pivot was centered on the ocular pupil. Further, it was demonstrated that by displacing the OCT beam eccentrically, the collected back-scattered intensity in HFL on the opposite side of the foveal pit increased, ostensibly due to more normal illumination there. Thus, they were able to demonstrate direct OCT visualization of HFL. However, the pupil entry position displacement was performed manually and was subject to patient motion artifacts. Furthermore, the lack of visual markers on the pupil renders acquiring multiple scans through the same entry location almost impossible. Pupil entry position may also play a critical yet underappreciated role in the geometrical accuracy of OCT retinal images. The often observed "tilt" of OCT retinal images with lateral displacement of the beam in the pupil is a reminder that OCT retinal images are subject to distortions depending upon many details of the patient's optical system, starting with the OCT beam entry position in the pupil. As quantitative metrics involving distances, areas and volumes derived from OCT images become more prevalent, it is expected that the geometrical accuracy of OCT images will become more important and careful control (or at least knowledge) of the beam trajectory through the patient's eye may become increasingly important.

Disclosed herein are automated systems and methods for controlling the lateral pupil entry position of retinal OCT by utilizing automated pupil tracking in conjunction with a 2D fast steering mirror placed conjugate to the retinal plane. Pupil tracking prevents lateral motion artifacts and vignetting from obscuring the desired pupil entry location. Furthermore, GPU-based, real-time RPE segmentation may be employed for quantifying apparent retinal tilt in the OCT B-scans as a function of pupil entry position.

Figure 10:
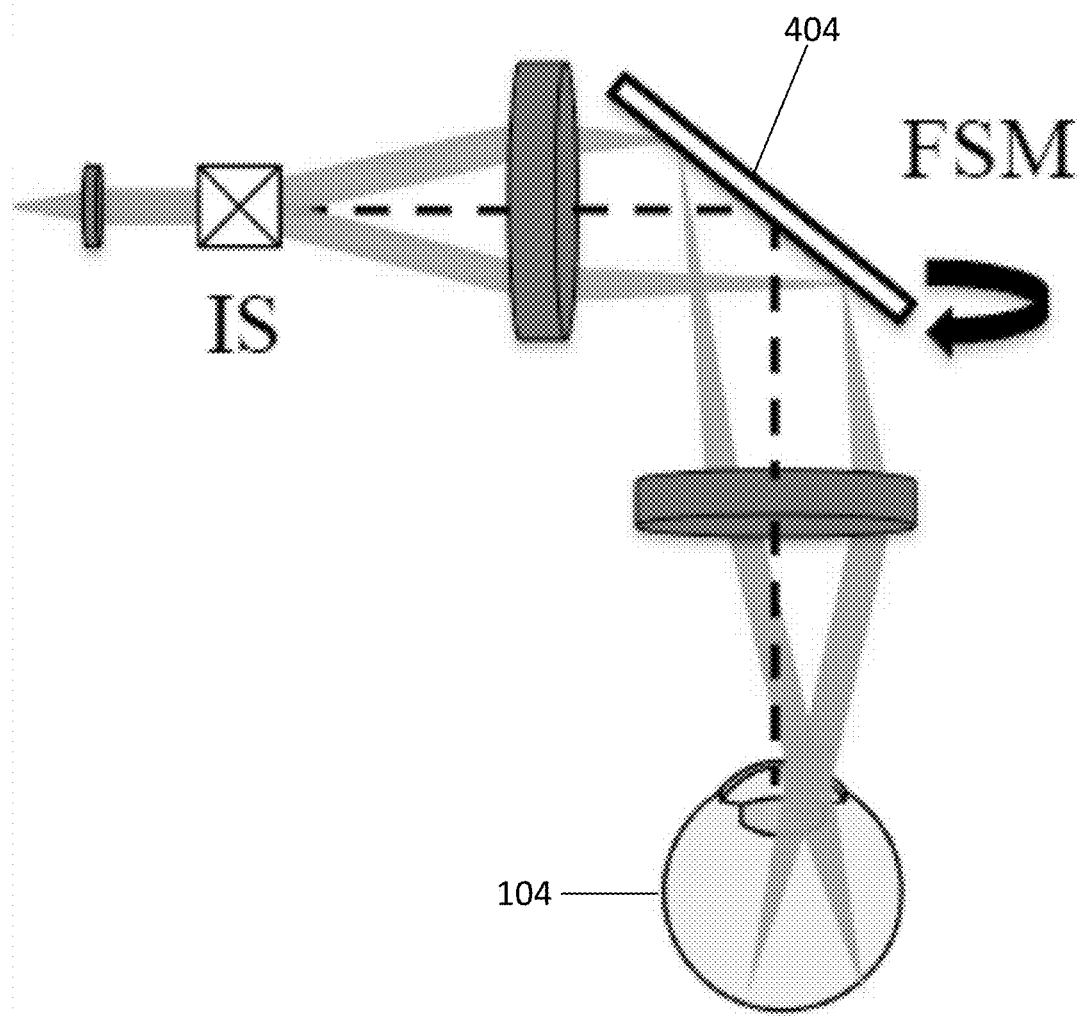
FIG. 10 is a schematic diagram of an example swept-source OCT system and scanning configuration that was utilized in experiments conducted in accordance with the present disclosure.

In accordance with embodiments, an example swept-source OCT system and scanning configuration that was utilized in experiments conducted in accordance with the present disclosure is illustrated in FIG. 10. The laser used was a commercial swept-frequency laser (Axsun Technologies, Inc.; Billerica, Mass.) centered at 1040 nm, with a tuning bandwidth of 100 nm and 100 kHz sweep rate, illuminated a Mach-Zender interferometer (as shown in FIG. 2 for example). The signal detection chain included a balanced photoreceiver (available from Thorlabs, of Newton, N.J.) and a digitizer operating at 800 MS/s (available from Alazar, of Quebec, Canada). Custom, GPU-based software was utilized for OCT acquisition at 100 kHz line rate. The sample arm is depicted in FIG. 10. As is typical in OCT retinal systems, a 4f lens system imaged a scanning galvanometer mirror pair into the pupil plane of the patient. However, a 2" diameter 2D fast steering mirror, with a bandwidth of 760 Hz (available from Optics in Motion LLC, of Long Beach, Calif.), was also placed at the Fourier plane of the objective lens, thus conjugate to the patient's retinal plane. Angular scanning of the FST resulted in lateral translation of the OCT scan pivot in the pupil as shown in FIG. 10. A dichroic mirror coupled the OCT sample arm and an IR camera (available from Point Grey, Inc., of Richmond, Calif.). IR pupil illumination at 850 nm enhanced the contrast between the iris and pupil and facilitated image processing. System performance was modeled in Zemax software (available from Zemax, LLC, of Redmond, Wash.).

Frames from the pupil camera were processed using binary morphology techniques to detect and track the center of the ocular pupil. The tracked lateral pupil motion was then converted to a voltage offset to drive the FSM to actively maintain the scan in the center of the pupil. In addition to motion compensation, pupil tracking and the FSM enabled automated lateral translation of the pupil entry position relative to the pupil center. Angular rotation of FSM was calibrated to correspond to lateral displacement at the pupil plane in millimeters. For quantification of apparent retinal tilt, our previously published automatic retinal segmentation using graph theory and dynamic programming was adapted for GPU-aided real time segmentation of RPE. The segmented RPE was then fitted to a line; angular tilt relative to the horizontal was calculated using the slope of the fitted line. To test our prototype system, SSOCT images of human volunteers were acquired. The sample arm optics depicted in FIG. 10 were mounted on a joystick-adjustable slit-lamp base to help with patient alignment.

Figure 11:
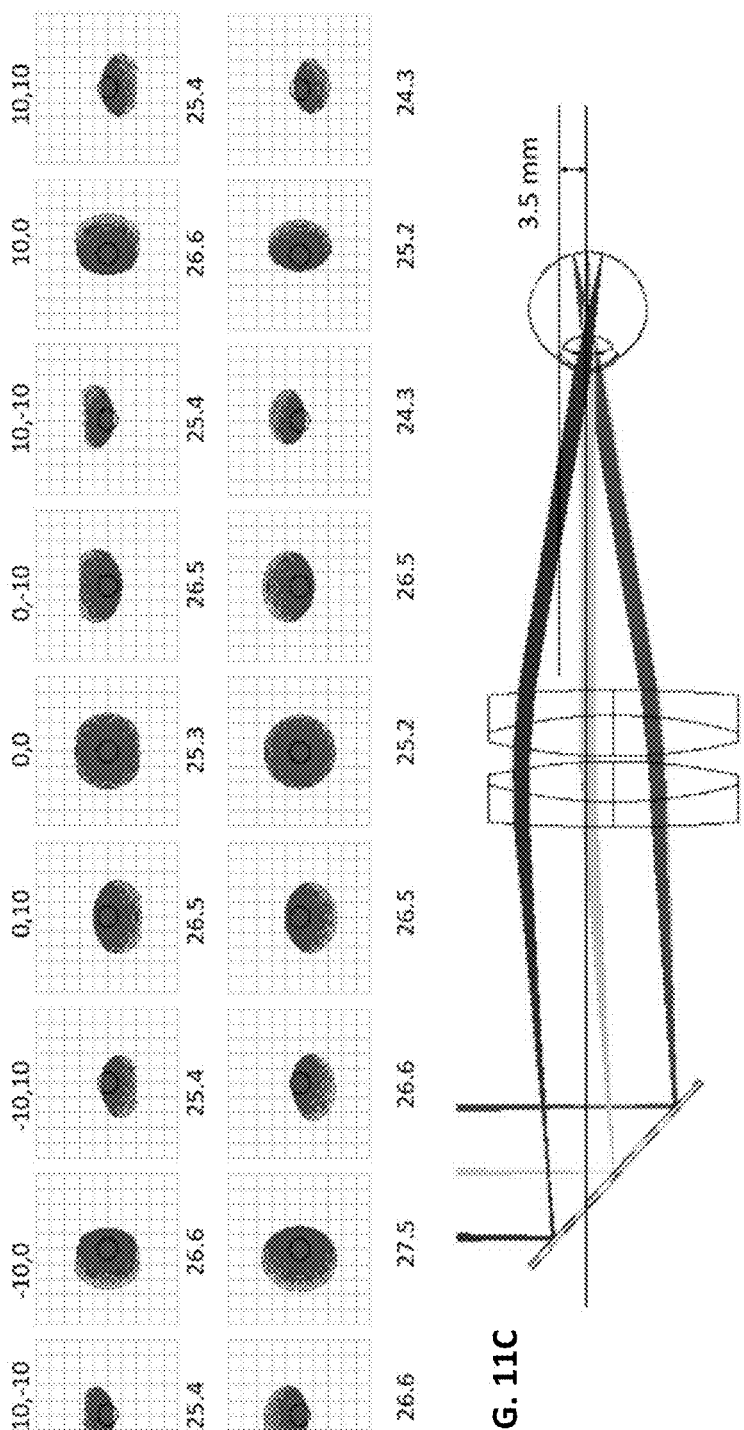
FIG. 11A shows predicted optical performance at the retinal plane of the eye model without any lateral offset for a +/−10 degree (optical) field of view.
FIG. 11B depicts the predicted optical performance of the system after lateral translation of the model eye and scan pivot by 3.5 mm.
FIG. 11C depicts an optical design model.

The optical performance of system, depicted in FIG. 10, was modeled in Zemax software using the schematic eye developed by Goncharov and Dainty. The FSM enabled a total lateral translation of +/−3.5 mm of the OCT scan pivot at the pupil plane, limited by the aperture of the dichroic mirror. FIG. 11A shows the predicted optical performance at the retinal plane of the eye model without any lateral offset for a +/−10 degree (optical) field of view. The geometric spot radii varied from 25.4 µm to 26.5 µm about the field of view. FIG. 11B depicts the predicted optical performance of the system after lateral translation of the model eye and scan pivot by 3.5 mm. The geometric spot radii varied from 24.3 µm to 27.5 µm. As evident, the optical performance did not degrade significantly even when the scanning beam is transmitted through a more peripheral region of the objective lens. FIG. 11C depicts an optical design model.

Figure 12:
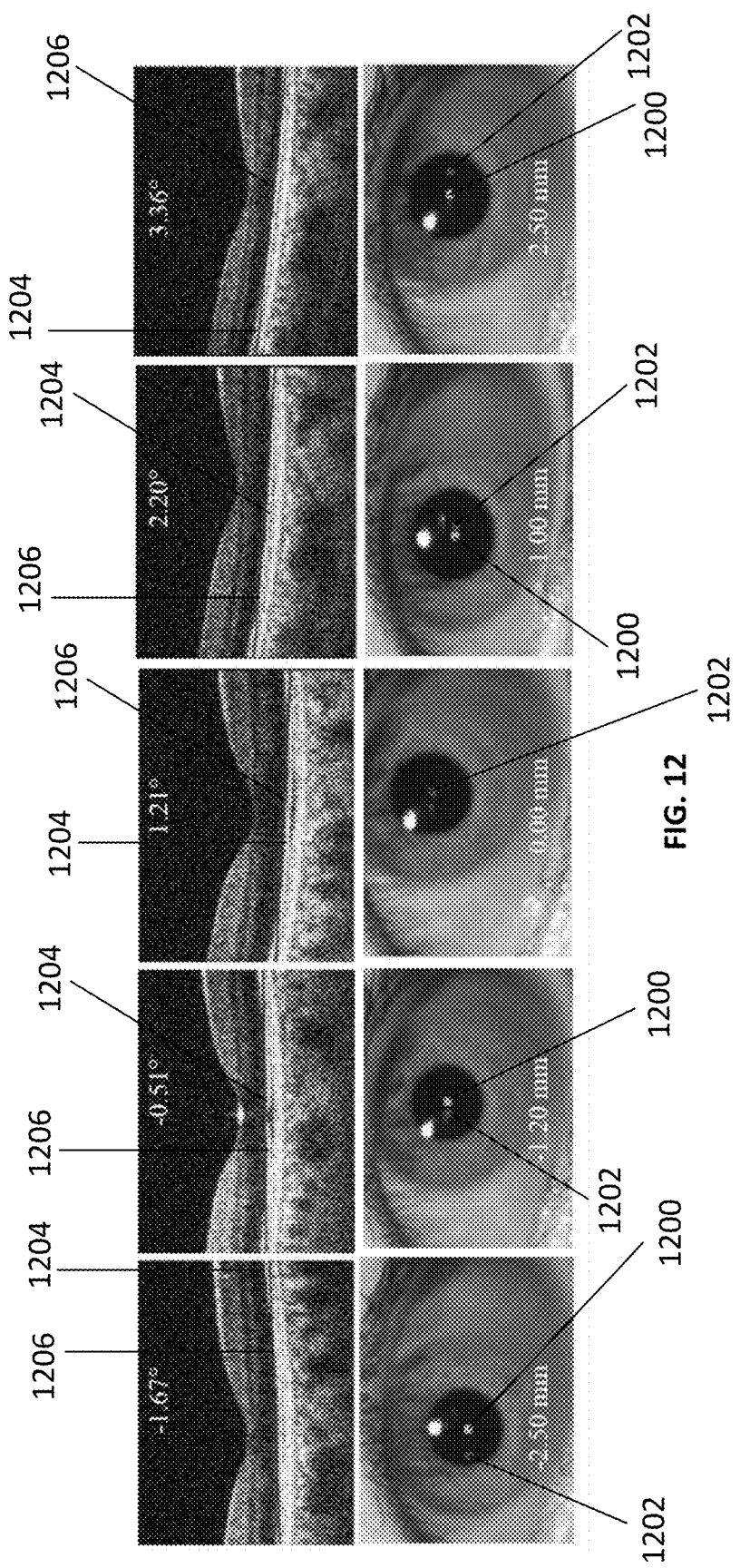
FIG. 12 shows single frame B-scans captured at different pupil entry positions.

A system in accordance with the present disclosure was tested on human volunteers. SSOCT B-scans, composed of 1000 A-lines, were acquired, processed and displayed at 100 Hz. Pupil tracking compensated for patient lateral motion and enabled controlled variation of the pupil entry position. GPU-aided RPE segmentation allowed for real-time calculation of apparent retinal tilt as a function of pupil entry position. Single frame B-scans captured at different pupil entry positions are shown in FIG. 12. In FIG. 12, varying pupil entry positions and measurement of apparent retinal tilt is demonstrated. The top row shows single-frame B-scans of the foveal pit. The bottom row shows corresponding pupil camera frames. Corresponding pupil camera frames are shown below. The dots 1200 and dots 1202 in the pupil camera frames correspond to the tracked center of the pupil and location of the OCT scan pivot, respectively. The pupil entry position was translated horizontally +/−2.5 mm relative to the tracked pupil center. The line 1204 in the OCT B-scans depicts the real-time segmented RPE; the line 1206 was the fitted line used to calculate apparent retinal tilt. The OCT fast scan axis was parallel to the scan pivot displacement. A fixation target was used to facilitate imaging of fovea. The patients' left eyes were imaged for all shown B-scans.

Translation of the scan pivot resulted in apparent retinal tilt. The +/−2.5 mm entry position translation resulted in an apparent retinal tilt of −1.67 to +3.36 degrees. It is noted that the when OCT beam entered through the pupil center (i.e., the OCT beam was aligned with the optical axis of the eye), the fovea appeared tilted. However, when the pupil entry position was offset by 1.2 mm nasally, the OCT B-scan of the fovea appeared flat. This finding may be attributed the angle between the visual and optical axis of the human eye. Because the foveal pit on not centered on the optical axis, it is reasonable to expect that the pupil entry position must be offset from the optical axis to achieve a flat fovea in the OCT B-scan. As discussed hereinabove, the apparent retinal tilt on the B-scan is not anatomically correct and instead is a function of several imaging parameters, including pupil entry position. A carefully designed eye model may be used to calculate OPL changes as a function of pupil entry position to corroborate our retinal tilt measurements.

HFL back-scattering intensity varies as a function of pupil entry position. Systems and methods disclosed herein enable direct visualization of HFL by varying pupil entry position eccentrically in a controlled manner. FIGS. 13A-13D shows two averaged (20×) B-scans acquired at different pupil entry positions. The pupil entry positions were 0 mm (FIG. 4C) and +2 mm (FIG. 4D) relative to the pupil center, corresponding to apparent retinal tilts of +1.20 and +3.20 degrees, respectively. As evident, the HFL was not visualized at a retinal tilt of +1.20 (FIG. 4A). However, the HFL was clearly visualized at a retinal tilt of +3.20 degrees (FIG. 4B).

Herein, systems and methods have been demonstrated for systematically controlling the pupil entry position of the OCT beam while mitigating lateral motion artifacts. Furthermore, automated method of determining apparent retinal tilt that can be utilized as feedback for automatic scanning of the scan pivot at the pupil plane have been described. Systems disclosed herein may facilitate OCT studies concerning directional sensitivity of retinal structures by automating translation of the pupil entry position.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. The embodiment was chosen and described in order to best explain the principles of the present disclosure and the practical application, and to enable others of ordinary skill in the art to understand the present disclosure for various embodiments with various modifications as are suited to the particular use contemplated.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An imaging system comprising:
    an eye tracking device configured to determine movement of an eye;
    an optical coherence tomography (OCT) apparatus configured to generate OCT images of a retina of the eye, and comprising a separate tracking scanner operable to maintain an OCT scan pivot within an ocular pupil during capture of the OCT images; and
    a controller configured to:
        control the tracking scanner to relocate the OCT scan pivot within the ocular pupil plane based on the determined movement of the eye, wherein the tracking scanner is relocated to be in a Fourier plane of the OCT optical apparatus for scanning of the retina;
        control the tracking scanner to maintain the OCT scan pivot to a center of the ocular pupil; and
        track the OCT scan pivot to another position within the ocular pupil for maximizing a source of contrast within an OCT retinal image.

2. The imaging system of claim 1, wherein the OCT apparatus comprises:
    an optical system comprising an imaging scanner to image a retinal plane; and
    a tracking scanner located in a plane conjugate to an OCT imaging plane.

3. The imaging system of claim 2, wherein the tracking scanner and imaging scanner are dual-axis optical scanners comprising at least one of a single mirror surface that can rotate in two dimensions (2D), a pair of single-axis galvanometer mirrors, and a 2D optical scanning device, wherein the tracking scanner and imaging scanner are configured to redirect an optical beam in two angular dimensions.

4. The imaging system of claim 1, wherein the controller is configured to control the separate tracking scanner to align the OCT scan pivot to a center of the ocular pupil based on the determined movement of the center of the ocular pupil.

5. An imaging system comprising:
    an eye tracking device configured to determine movement of an eye;
    an optical coherence tomography (OCT) apparatus configured to generate OCT images of an anterior segment of the eye, and comprising a tracking scanner operable to maintain an OCT scan fixed with respect to an ocular pupil during capture of the OCT images; and
    a controller configured to:
        control the tracking scanner to relocate the OCT scan within an ocular pupil plane based on the determined movement of the eye, wherein the tracking scanner is relocated to be in a Fourier plane of the OCT optical apparatus for scanning of the retina;
        control the tracking scanner to maintain the OCT scan pivot to a center of the ocular pupil; and
        track the OCT scan pivot to another position within the ocular pupil for maximizing a source of contrast within an OCT retinal image.

6. The imaging system of claim 5, wherein the eye tracking device comprises a camera configured to capture a sequence of images of the ocular pupil and a light source for illuminating the ocular pupil.

7. The imaging system of claim 5, wherein the OCT apparatus comprises:
    a low-coherence light source;
    an optical lens positioned downstream from the light source to receive light from the light source;
    an imaging scanner positioned downstream from the optical lens to receive the light through the optical lens; and
    a tracking scanner located in a plane conjugate to the ocular pupil plane.

8. The imaging system of claim 5, wherein the controller is configured to:
    identify the ocular pupil;
    process a sequence of images of the movement of the ocular pupil;
    analyze the sequence of images of the ocular pupil to determine an offset; and
    position the tracking scanner based on the offset.

9. A method comprising:
    using an eye tracking device to track a movement of an ocular pupil;
    calculating the movement of the ocular pupil;
    correcting for a lateral motion of the ocular pupil via a measured offset;
    using the correction for the lateral motion of the pupil to obtain motion-corrected images of the ocular retina;
    relocating the tracking scanner to be in a Fourier plane of an optical coherence tomography (OCT) optical apparatus for scanning of the retina;
    controlling the tracking scanner to maintain the OCT scan pivot to a center of the ocular pupil; and
    track the OCT scan pivot to another position within the ocular pupil for maximizing a source of contrast within an OCT retinal image.

10. The method of claim 9, wherein tracking the movement of the ocular pupil comprises:
    identifying the ocular pupil via an imaging system that comprises the OCT apparatus, a tracking scanner, an imaging scanner, a light source, and a controller; and
    capturing a sequence of images of the ocular pupil via a camera.

11. The method of claim 10, wherein the imaging scanner comprises a reflective surface positioned to direct a reflected light onto a position within the ocular pupil, and wherein the method further comprises:
    using a light source to illuminate the ocular pupil, the light source being positioned at a side that opposes the reflective surface; and
    using a camera to capture a sequence of images of the ocular pupil, the camera being positioned at the side that opposes the reflective surface.

12. The method of claim 9, wherein the measured offset is determined based on the movement of the ocular pupil, and
wherein the method further comprises:
capturing a plurality of image sequences of the movement of the ocular pupil via a camera;
comparing the image sequences to calculate the movement of the ocular pupil relative to a previously captured image in the sequence;
producing an output based on the calculated movement that comprises an offset; and
converting the output offset into a set of voltage offsets.

13. The method of claim 9, wherein correcting for the lateral motion of the ocular pupil via the voltage offset comprises:
moving a tracking scanner based on a set of the voltage offsets to realign an OCT scan pivot of the OCT apparatus with a center of the ocular pupil; and
in response to moving the tracking scanner, providing a lateral compensation for the movement of the center of the ocular pupil.

14. The method of claim 9, further comprising:
passing light through an optical lens onto a dichroic mirror for reflection onto a center of the ocular pupil;
illuminating the center of the ocular pupil via the reflected light from the dichroic mirror;
imaging the center of the ocular pupil via a camera; and
capturing a plurality of image sequences of the movement of the center of the ocular pupil.

\* \* \* \* \*